United States Patent [19]

Spector

[11] 4,277,024
[45] Jul. 7, 1981

[54] SELF-STICK AROMA-DISPENSING TAB

[76] Inventor: Donald Spector, 380 Mountain Rd., Union City, N.J. 07087

[21] Appl. No.: 971,380

[22] Filed: Dec. 20, 1978

[51] Int. Cl.³ .............................................. A61L 9/04
[52] U.S. Cl. ..................................... 239/36; 206/466; 239/56
[58] Field of Search ....................... 239/36, 53, 55, 56; 40/124.2, 19.5; 206/466

[56] References Cited

U.S. PATENT DOCUMENTS

| 2,615,754 | 10/1952 | Lindenberg | 239/36 |
| 3,441,353 | 4/1969 | Claff | 239/36 X |
| 3,575,345 | 4/1971 | Buck, Jr. | 239/36 X |
| 3,896,995 | 7/1975 | Lelicoff | 239/36 |
| 4,145,001 | 3/1979 | Weyenberg et al. | 239/56 |
| 4,158,440 | 6/1979 | Sullivan et al. | 239/56 X |

FOREIGN PATENT DOCUMENTS 126358   1/1948   Australia ................................. 206/466

Primary Examiner—Andres Kashnikow
Attorney, Agent, or Firm—Michael Ebert

[57] ABSTRACT

An aroma-dispensing tab that is stickable onto any surface, such as an article of apparel, to exude a pleasant fragrance or to function as an insect repellent. The tab is in the form of a sac constituted by a base having a perforated dome marginally secured thereto to define a vented chamber occupied by an absorbent pad saturated by a liquid scent. A layer of pressure-sensitive adhesive on the underside of the base makes it possible to attach the tab to any surface.

1 Claim, 6 Drawing Figures

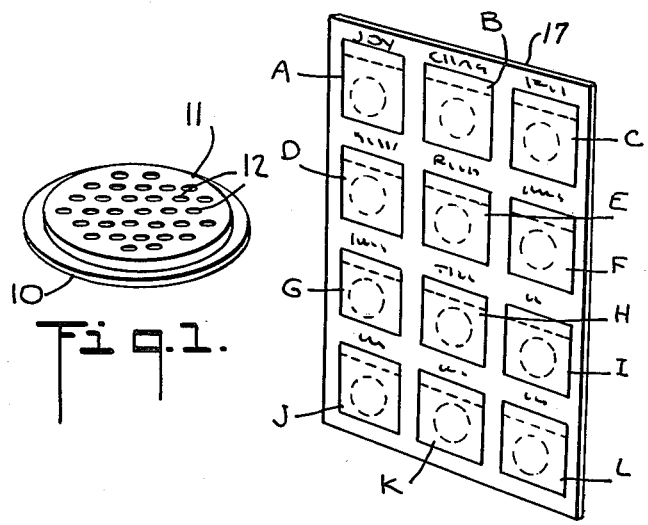
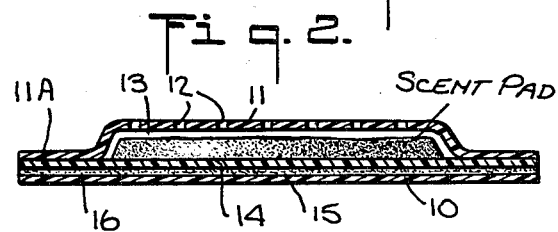
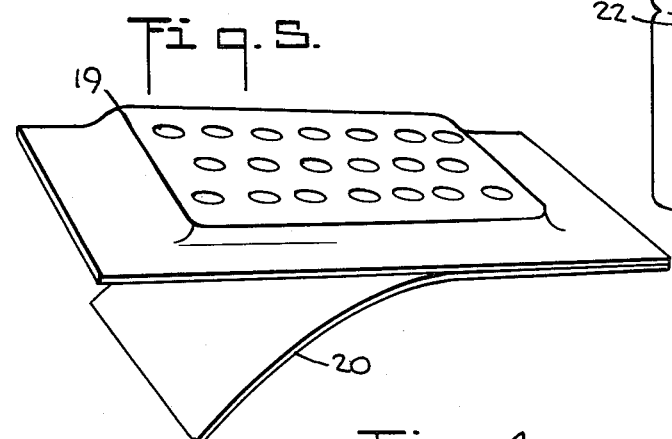
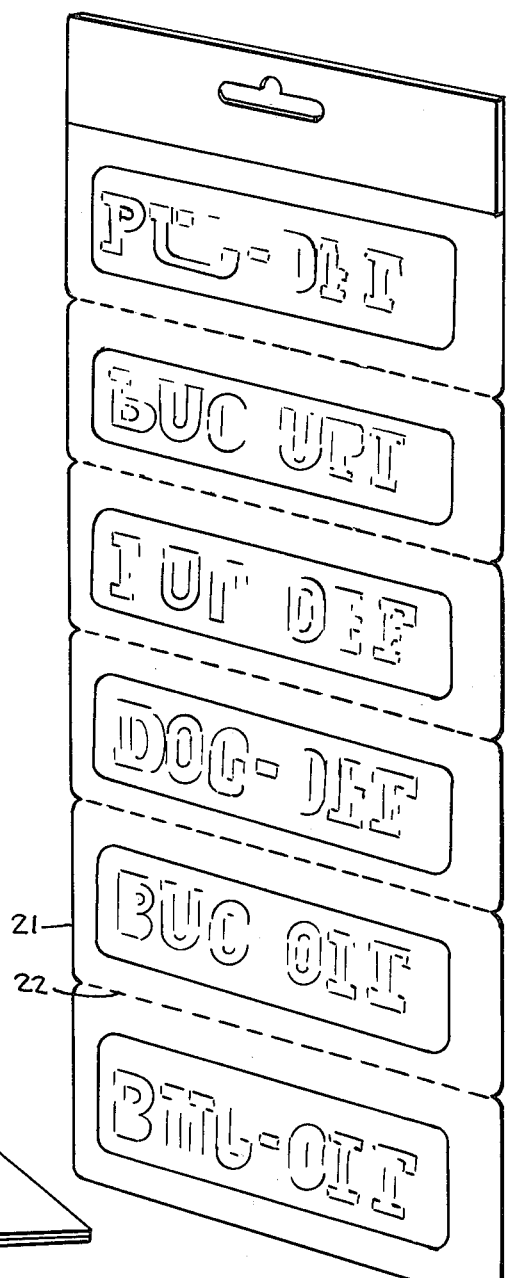
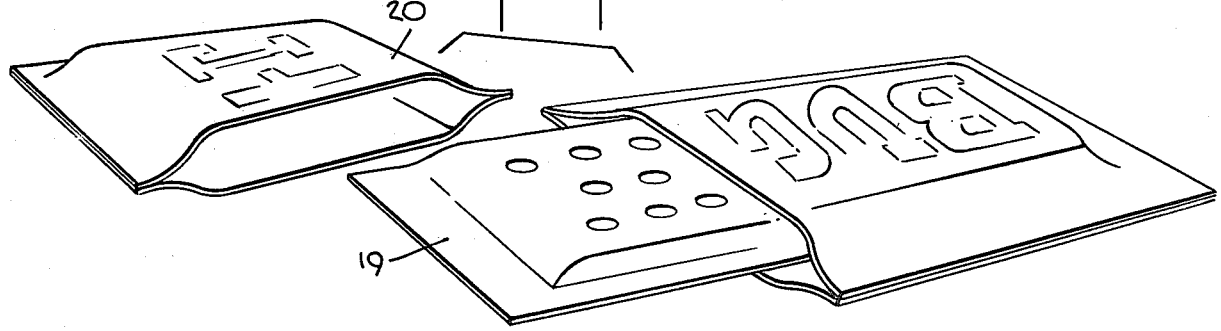

SELF-STICK AROMA-DISPENSING TAB

BACKGROUND OF INVENTION

This invention relates generally to aroma dispensers, and in particular to an aroma-dispensing tab that is stickable onto any surface.

As used herein, the term "aroma" is not limited to pleasant or savory smells but encompasses scents that function as insecticides, animal-repellents, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with alcohol.

Perfumes and perfume-based products are generally sprinkled, sprayed, rubbed or otherwise directly applied to the skin of the wearer. Because skin sensitivity is a highly individual characteristic and differs from person to person, when formulating and testing a perfume-based product, the manufacturer must run extensive tests on toxicity, dermatological irritation and allergenic reactions over a broad range of skin types. But even a product that is found to be non-reactive with all but a small percentage of typical skin types, may still not be commercially acceptable and create problems of product liability.

It is for this reason that the typical manufacturer confines his product line to those perfume-based products which have a proven record of acceptability, the manufacturer making no use of any solvent other than alcohol. This imposes tight restrictions on the available range of fragrances for personal use; for it precludes those natural and synthetic scents which, though highly pleasing, are nevertheless reactive with some skin types. Also excluded are scents which require or function best with solvents other than alcohol. Since the concentration and properties of the solvent govern the dissipation and persistence characteristics of the perfume, this prohibition rules out the possibilities for dissipation time control offered by non-alcoholic solvents.

Perfumes and perfume-based liquid scents are presently contained in bottles or spray-dispensers in various sizes, usually graded in fractions of an ounce. When such bottles are stored on a shelf, there is no problem of spillage; but when the user carries the bottle or vial in a purse, which is subject to jostling, one cannot be sure that it will not leak.

Moreover, while a user will normally apply a perfume of a given type to the skin to produce a fragrance suitable for outdoor use, say, on a warm afternoon, a fragrance of a different character may be more appropriate for indoor evening wear; and still another for another occasion on the same day. Yet it is not usually feasible for a user to carry several vials of perfume in her purse to satisfy all of these daily requirements.

Another factor that comes into play with liquid perfumes in the form of which they are presently dispensed is the matter of sampling. In determining whether a given perfume is to the taste of the user, a small sample is applied to the back of the hand so that the tester can smell it. But the momentary impression made by this test which typically takes place at the counter of a store is inadequate, and unless the user actually wears the perfume for at least a day in a variety of environments, the user's reaction is uncertain. Thus whether a perfume is excessively heavy or pungent in the judgment of a given user cannot be ascertained merely by briefly smelling a sample.

On the other hand, should a consumer, on the basis of hand sampling, set aside, say, five perfumes out of a choice of twelve as being of interest, then under present marketing practices, the consumer would have to buy five vials of the selected perfumes so that she could then actually put each to use before reaching a conclusion as to her true preferences. Since quality perfumes, even in the smallest bottles, are quite expensive, this test procedure is not one many consumers can afford.

An obvious solution to many of the above-identified problems is to provide a perfume that is not applied to the skin but which emits a fragrance in the proximity of the wearer. To this end, it is known to make use of sachets; that is, small bags containing a perfumed powder which serves to scent clothes. By placing a sachet in a clothes closet or drawer, the perfumes will permeate the clothing contained therein, and the perfume will linger when the article of apparel is worn.

But this approach has many drawbacks; for the range of perfumes that lend themselves to powdered or sachet form is very limited and does not, in practice, go much beyond a lavender fragrance. Moreover, one cannot carry a sachet on the person, for these are designed to scent clothing in a confined space.

SUMMARY OF INVENTION

In view of the foregoing, the main object of this invention is to provide a self-stick aroma-dispensing tab that may be applied to any suitable site, such as under the collar of a shirt or under the arm of a dress to exude any desired fragrance.

A significant advantage of a tab of the above type is that it obviates all of the dermatological drawbacks associated with standard liquid scents applied directly to the skin; for while the tab can be in close proximity to the skin, it is not in physical contact therewith. Thus it becomes possible to formulate perfumes using solvents and synthetics which heretofore were dermatologically interdicted, and thereby enormously expand the spectrum of available personal scents.

More particularly, it is an object of the invention to provide a self-stick tab in which a perfume-saturated pad is enveloped within a perforated sac which is adherable to a desired site and which, for a prolonged period, exudes an aroma having a selected characteristic. Thus the aroma may be a pleasing fragrance, or an insect or animal repellent.

Yet another object of the invention is to provide a self-stick aroma-dispensing tab that is wrapped in a hermetically sealed foil package that prevents emission of the aroma until the package is ruptured and the tab applied to a given site.

One important aspect of the present invention from the commercial standpoint is that it makes available to the typical consumer, at a relatively low cost, highly-expensive perfumes which are otherwise outside the consumer's affordability range; for each tab includes only a small and therefore inexpensive quantity of the costly perfume. In this way, a consumer can try out and put to use perfumes which she cannot afford to buy in standard vial form.

A salient feature of the invention is that a group of packaged tabs, each giving off a distinct aroma, may be identified and mounted on a low-cost sampler card so that a consumer can try out and use as many as ten to twenty different perfumes without having to purchase separate bottles thereof.

Briefly stated, these objects are attained in a self-stick aroma-dispensing tab constituted by a sac formed by a base and a perforated dome adhered to the periphery thereof to define a vented chamber which houses a pad of absorbent material saturated with a liquid scent or other aroma-producing liquid. The base of the tab has a layer of pressure-sensitive adhesive secured thereto which is protectively covered by a peel-off sheet. The tab is hermetically sealed in a rupturable foil package which prevents evaporation from the pad and the emission of an aroma during storage. By removing the package and peeling off the cover sheet, one may then apply the tab to any suitable site.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a first embodiment of a self-stick aroma-dispensing tab in accordance with the invention;

FIG. 2 is a section taken through the tab shown in FIG. 1;

FIG. 3 is a sampler card containing a set of tabs of the FIG. 1 type;

FIG. 4 is a perspective of a second embodiment of a tab in accordance with the invention, the tab being sealed in a foil package which is partly removed;

FIG. 5 shows the tab of FIG. 4 with its cover sheet being peeled off; and

FIG. 6 shows a strip of tabs, the strip being defined by packaging foil common to all tabs.

DESCRIPTION OF THE INVENTION

First Embodiment

Referring now to FIGS. 1 and 2, there is shown a button-shaped, self-stick, aroma-dispensing tab in accordance with the invention, the tab being constituted by a sac formed of a disc-shaped base 10 having marginally bonded thereto a flat-top dome 11 provided with an array of perforations 12 to define a vented chamber 13.

In practice, base 10 and dome 11 may be formed of flexible, synthetic plastic film material, such as polyethylene or PVC, the flanged margin 11A of dome 11 being thermally or otherwise bonded to the circular border of the base. Housed within chamber 13 is a wafer or pad 14 of absorbent material which may be a cellulose blotter, a flexible foam plastic or any other sponge-like, non-reactive substance. The pad is saturated with a concentrated liquid scent of the desired character, so that a small supply of the liquid is capable of giving off a scent for a prolonged period. The underside of base 10 is provided with a layer 15 of pressure-sensitive material which is protectively covered by a peel-off sheet 16.

Because chamber 13 is vented, the scented liquid is permitted to evaporate to discharge a fragrance into the atmosphere. Hence in order to prevent such evaporation and render the pad inactive until it is put to use, the entire tab is wrapped in a sealed envelope which, in practice, may be a metal foil-plastic laminate package which provides a hermetic seal until the package is ruptured.

As pointed out previously, because the liquid scent is not applied to the skin, its formulation need not take skin sensitivity into account. Use may be made, therefore, of those scent-producing ingredients, fixatives and solvents that produce any desired aroma without regard to allergenic reaction or other dermatological factors. Thus the tab lends itself to the inclusion of highly powerful, yet pleasing scents which cannot safely be brought into contact with the skin.

When, for example, the aroma is that of a male cologne, the tab may be applied to the rear of the wearer's shirt collar and thereby rendered invisible. But because this button-shaped tab is relatively inconspicuous, it may be placed anywhere on the wearer's clothing or dress. The tab may be fabricated with a sac having a neutral color to enhance its inconspicuous character, or it may be made in colorful or striking designs to afford a design accent when applied, say, to the front of a blouse rather than under the arm of a dress. The tabs may also be used as sachets and attached to clothing stored in drawers and closets.

Because the amount of perfume in each tab is very small, the cost per tab is low. Thus one can, from an expensive one-ounce bottle of perfume, derive a sufficient charge for hundreds of pads and thereby make available to a consumer a low-cost tab of a very costly perfume.

In practice, the consumer may be offered, as shown in FIG. 3, a sampler card 17 having secured thereto an array of tab packages, each containing a distinct, well-known branded perfume. The foil packages in this instance are rectangular envelopes A, B, C, D, etc., which contain the button-shaped tabs, the upper margin of the envelope being stapled or otherwise attached to card 17. The margin is perforated, making it possible for the consumer to rip off any tab, the margin remaining attached to the card.

One can also attach such foil-packaged tabs to greeting cards such that the greeting is accompanied by a gift that will be appreciated by the recipient. Also, for promotional purposes, an advertiser may mail packaged tabs to magazine or other subscribers and thereby make it possible for a prospect to actually try out the advertised perfume.

Or one could even secure a packaged tab to the cover page or an inside sheet of a magazine, in which case it may be desirable to provide a tab in a more flattendd form than that shown in FIG. 2. This flattened tab may take the form of a perfume-saturated blotter sheet sandwiched between a base sheet and a perforated face sheet, which in turn is covered by a peel-off cover sheet. Thus instead of a wrapper enveloping the entire tab, only the tab holes are sealed off.

Second Embodiment

Referring now to FIGS. 4 and 5, there is shown a tab 19 which is essentially the same as the first embodiment and includes a base and a perforated dome to define a vented chamber housing a liquid scent-saturated pad, except that the form of the tab is tablet-like. Tab 19 is sealed in a foil package 20 having a corresponding formation.

The tab has a larger capacity than the button-like tab shown in FIGS. 1 and 2, and may therefore be used for insect or animal repellents. Thus a tab of this type may be attached to a sleeping bag or a camping tent, or even applied to walking shorts. Because the repellent is not in physical contact with the skin, one can use stronger insect-repelling ingredients than are tolerable by the skin. Hence the tab can be effective in repelling insects in the general region in which the tab is installed rather than in a small zone adjacent the skin, as wit conventional skin-applied repellents.

When the tab includes a repellent effective against dogs, cats or other animals, the tab may be applied to couches or other household articles which one wishes to protect against mutilation by animals.

In practice, as shown in FIG. 6, a tap strip 21 may be formed by sandwiching a row of tabs between two sheets of packaging foil which are laminated together, lines 22 of perforation being drawn between the tabs in the row, thereby providing individual tear-off packages 20 which are separable from the strip.

While there have been shown and described preferred embodiments of a self-stick aroma-dispensing tab in accordance with the invention, it will be appreciated that many changes and modifications may be made therein without, however, departing from the essential spirit thereof.

I claim:

1. A perfume sampler constituted by a card having an array of individually removable, hermetically-sealed, rupturable metal foil plastic laminate packages thereon having a rectangular form and separate from each other, each housing an aroma-dispensing button-shaped tab that is removable from the ruptured package and is stickable onto any surface, each of said tabs comprising:

A. a sac of synthetic plastic material non-reactive with liquid perfume and formed by a base having a perforated dome marginally secured thereto to define a vented chamber, said base having a pressure-sensitive adhesive layer on its underside covered by a peel-off sheet; and B. an absorbent pad disposed in said chamber saturated with a liquid perfume scent to exude a desired aroma through the perforated dome when the tab is removed from its hermetically-sealed package, the pads in the array of packages having different scents which are identified on the packages so that a consumer can try out the various scents without having to purchase separate bottles thereof.

* * * * *